(12) United States Patent
Trout, III et al.

(10) Patent No.: US 7,322,943 B2
(45) Date of Patent: Jan. 29, 2008

(54) APPARATUS AND METHOD FOR THE MULTI-AXIAL PLACEMENT OF SURGICAL FASTENERS

(75) Inventors: Hugh H. Trout, III, Bethesda, MD (US); Howard M. Tanner, Logan, UT (US)

(73) Assignee: EVA Corporation, Bethesda, MD (US)

( * ) Notice: Subject to any disclaimer, the term of this patent is extended or adjusted under 35 U.S.C. 154(b) by 740 days.

(21) Appl. No.: 10/323,661

(22) Filed: Dec. 20, 2002

(65) Prior Publication Data

US 2003/0167066 A1 Sep. 4, 2003

Related U.S. Application Data

(60) Provisional application No. 60/341,852, filed on Dec. 21, 2001.

(51) Int. Cl.
*A61B 5/00* (2006.01)
(52) U.S. Cl. .................................................. 600/585
(58) Field of Classification Search ................ 600/104, 600/107, 139, 585; 606/46, 47, 49; 604/20, 604/501
See application file for complete search history.

(56) References Cited

U.S. PATENT DOCUMENTS 4,474,174 A * 10/1984 Petruzzi ...................... 600/104
4,562,596 A    1/1986 Kornberg
4,787,899 A   11/1988 Lazarus
4,925,268 A *  5/1990 Iyer et al. ...................... 385/12
5,042,707 A    8/1991 Taheri
5,104,392 A    4/1992 Kittrell et al.
5,350,375 A    9/1994 Deckelbaum et al.
5,596,988 A *  1/1997 Markle et al. ............... 600/353
6,219,577 B1 * 4/2001 Brown et al. ................. 604/20
6,270,492 B1   8/2001 Sinofsky

* cited by examiner

*Primary Examiner*—Kevin T. Truong
(74) *Attorney, Agent, or Firm*—John N. Coulby; Kelley Drye & Warren, LLP

(57) ABSTRACT

Several embodiments of a penetration apparatus and methods for using the same during a surgical procedure are disclosed. The penetration apparatus comprises a thin elongated body having a first end, a second end, and a central longitudinal axis extending there between. The first end opposes the second and is aligned within a vessel matrix during the surgical procedure. The second end of the body is substantially free and may be rotated around the axis. The penetration apparatus may also be housed within a catheter that has a cavity that precisely accommodates the penetration apparatus. Activation and advancement of the penetration apparatus within the catheter forms an incision through a vessel matrix enabling the placement of a fastener or a plurality of fasteners therein.

38 Claims, 8 Drawing Sheets

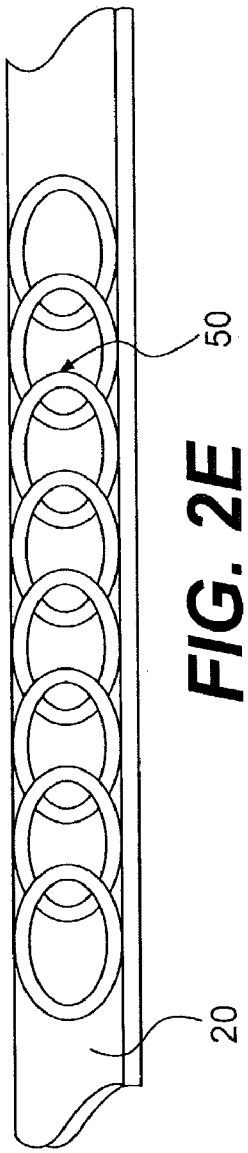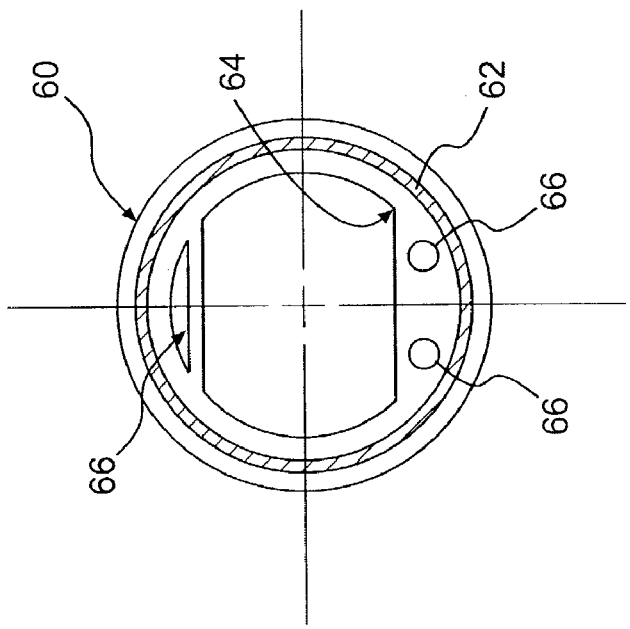

APPARATUS AND METHOD FOR THE MULTI-AXIAL PLACEMENT OF SURGICAL FASTENERS

CROSS-REFERENCE TO RELATED APPLICATIONS

The present inventions relate to, and are entitled to the benefit of the earlier filing date and priority of, U.S. Provisional Patent Application 60/341,852, filed Dec. 21, 2001.

FIELD OF THE INVENTION

The present inventions relate to surgical instruments and in particular, to a penetration apparatus and methods for the positioning of the same. More particularly, the present inventions relate to a multi-axial penetration apparatus embodying a thin, elongated body for the creation of an incision within a vessel matrix.

BACKGROUND OF THE INVENTION

An aneurysm is a ballooning of the wall of an artery resulting from weakening of the artery due to disease or other conditions. Left untreated, the aneurysm will frequently rupture, resulting in loss of blood and death.

Aortic aneurysms are the most common form of arterial aneurysm and are life-threatening. The aorta is the main artery which supplies blood to the circulatory system. The aorta arises from the left ventricle of the heart, passes upward and bends over behind the heart, and passes down through the thorax and abdomen. Among other arterial vessels branching off the aorta along its path, the abdominal aorta supplies two side vessels, the renal arteries to the kidneys. Below the level of the renal arteries, the abdominal aorta continues to about the level of the fourth lumbar vertebrae (or the navel), when it divides into the iliac arteries, in turn, supply blood to the lower extremities and perineal region.

It is common for an aortic aneurysm to occur in that portion of the abdominal aorta between the renal arteries and iliac arteries. An aortic aneurysm larger than about 5 cm in diameter in this section of the aorta is ominous. Left untreated, the aneurysm may rupture resulting in rapid, and usually fatal, hemorrhaging. Typically, a surgical procedure is not performed on aneurysms smaller than 5 cm because no statistical benefit exists in performing such procedures.

Aneurysms in the abdominal aorta are associated with a particularly high mortality rate; current medical standards call for urgent operative care. Abdominal surgery however, results in substantial stress to the body. Although the mortality rate for an aortic aneurysm is extremely high, there is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm form the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Further the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

In recent years, methods have been developed to attempt to treat an aortic aneurysm without the attendant risks of intra-abdominal surgical intervention. Among them are inventions disclosed and claims in Kornberg, U.S. Pat. No. 4,562,596 for Aortic Graft, Device and Method for Performing an Intraluminal Abdominal Aortic Aneurysm Repair; Lazarus, U.S. Pat. No. 4,787,899 for Intraluminal Graft Device, System and Method; and Taheri, U.S. Pat. No. 5,042,707 for Intravascular Stapler, and Method of Operating Same.

Although in recent years certain techniques have been developed that may reduce the stress, morbidity, and risk of mortality associated with surgical intervention to repair aortic aneurysms, including delivery catheter assemblies, none of the systems that have been developed provide an apparatus for the multi-axial placement of surgical fasteners through a delivery catheter. What is therefore needed is an apparatus that can be used by an interventionist outside the body to effectively create an incision in the repair member and the tissue, as distinct from a hole. Additionally, the apparatus should be capable of deploying fasteners for securing the repair member to the tissue. Further, there is a need to provide for minimal intrusiveness during repair of an aortic aneurysm.

Additional advantages of various embodiments of the invention are set forth, in part, in the description that follows and, in part, will be apparent to one of ordinary skill in the art from the description and/or from the practice of the invention.

SUMMARY OF THE INVENTION

Responsive to the foregoing challenges, the present invention is directed to a penetration apparatus for use during a surgical procedure, comprising: a thin elongated body having a first end, a second end, and a central longitudinal axis; the first end opposes the second end on the body and is aligned with a vessel matrix during the surgical procedure; the second end is substantially free; and the longitudinal axis spans the body from the first to the second end wherein the body rotates about the axis for placement of an incision within the vessel matrix. The apparatus may further comprise at least one fastener coupled to the body. The apparatus may also include a fastener assembly with at least one fastener.

The present invention is also directed to a catheter derivative comprising a catheter with at least one cavity and a penetration apparatus positioned therein, the penetration apparatus comprising a thin elongated body having a first and a second end and a central longitudinal axis; the first end opposes the second end on the body and is aligned within a vessel matrix during the surgical procedure; the second end is substantially free; and the longitudinal axis spans the body from the first to the second end wherein the body rotates about the axis for placement; wherein the penetration apparatus is slideably housed within the cavity of the catheter.

The present invention is also directed to a method of using a penetration apparatus for use during a surgical procedure, comprising: positioning the penetration apparatus within a vessel; and activating and advancing the penetration apparatus to form an incision in the vessel matrix. The method of use may also further comprise the step of coupling a fastener to the penetration apparatus wherein the fastener surrounds a cross-section of the penetration apparatus; and deploying the fastener through the incision in the vessel matrix.

Yet another method of use is directed to a method of using a penetration apparatus with a catheter derivative during a surgical procedure, which comprises the steps of: inserting the penetration apparatus into the catheter; positioning the catheter within a vessel matrix; activating and advancing the penetration apparatus through the catheter in the vessel matrix; and withdrawing the penetration apparatus. The method also further comprise advancing a thin walled sheath of the catheter derivative through the vessel matrix prior to activating and advancing the penetration apparatus. The method, wherein the penetration apparatus has at least one fastener, may also further comprise the step of deploying the fastener through an incision in the vessel matrix prior to withdrawing the penetration apparatus. The method, wherein the catheter derivative has a fastener assembly, may also further comprise the step of activating and advancing the fastener assembly through the catheter after withdrawing the penetration apparatus; and deploying a fastener through an incision in the vessel matrix.

The present invention is further directed to a method of placing at least one fastener during a surgical procedure, which comprises the steps of: gaining access to a surgical site with a catheter derivative; positioning the catheter derivative within a vessel matrix; inserting a penetration apparatus into the catheter; activating and advancing the penetration apparatus to form a treatment specific incision in the vessel matrix; and deploying a fastener through the incision of the vessel matrix. The method may also further comprise the step of inserting a fastener assembly into the catheter after inserting the penetration apparatus; withdrawing the penetration apparatus prior to deploying the fastener; and activating and advancing the fastener assembly within the vessel matrix.

It is to be understood that both the foregoing general description and the following detailed description are exemplary and explanatory only, and are not restrictive of the invention as claimed. The accompanying drawings, which are incorporated herein by reference, and which constitute part of this specification, illustrate certain embodiments of the invention and together with the detailed description, serve to explain the principles of the present invention.

BRIEF DESCRIPTION OF THE DRAWINGS

In order to assist the understanding of the present invention, reference will now be made to the appended drawings, in which like reference characters refer to like elements.

FIG. 2E is a planar representation of fasteners as illustrated in FIG. 2D when positioned about the penetration apparatus.

FIG. 3A illustrates a cross-sectional view of a catheter derivative having the capacity to house a preferred embodiment of the present invention.

DETAILED DESCRIPTION OF EMBODIMENTS OF THE INVENTION

Figure 1A:
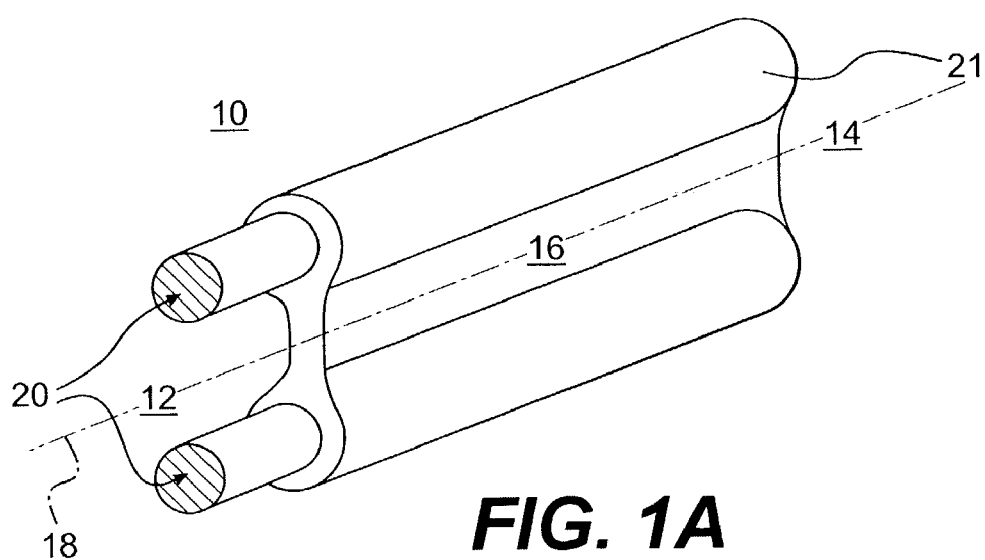
FIGS. 1A, 1B, 1C, and 1D, are side and cross-sectional views of preferred embodiments of the penetration apparatus.
Figure 1B:
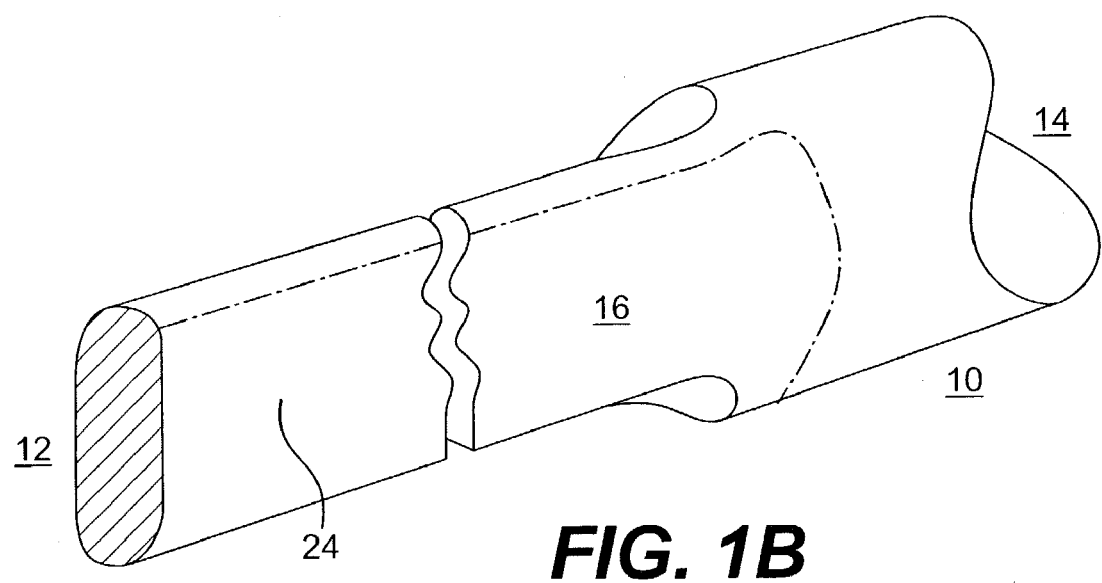

Various preferred and exemplary embodiments of the penetration apparatus of the present invention and the method of use thereof are described in further detail with reference to the figures. Similar reference numbers are used throughout the figures for like elements or components of the invention. It is understood that those skilled in the relevant art will appreciate that the present invention has applications in various other surgical procedures.

Penetration Apparatus

Preferred embodiments of the penetration apparatus 10 are shown in FIGS. 1A, 1B, 1C, and 1D. The penetration apparatus 10 has a first end 12 and a second end 14. A thin elongated body 16 connects the first end 12 and the second end 14 to form a unitary structure of the penetration apparatus 10. The penetration apparatus 10 may be configured and actuated to form a treatment specific incision 300. The thin elongated body 16 may be of, but is not limited to, a solid or tubular, uniaxial or multi-axial, oblong, elliptical, wedged or tapered configuration.

Figure 1C:
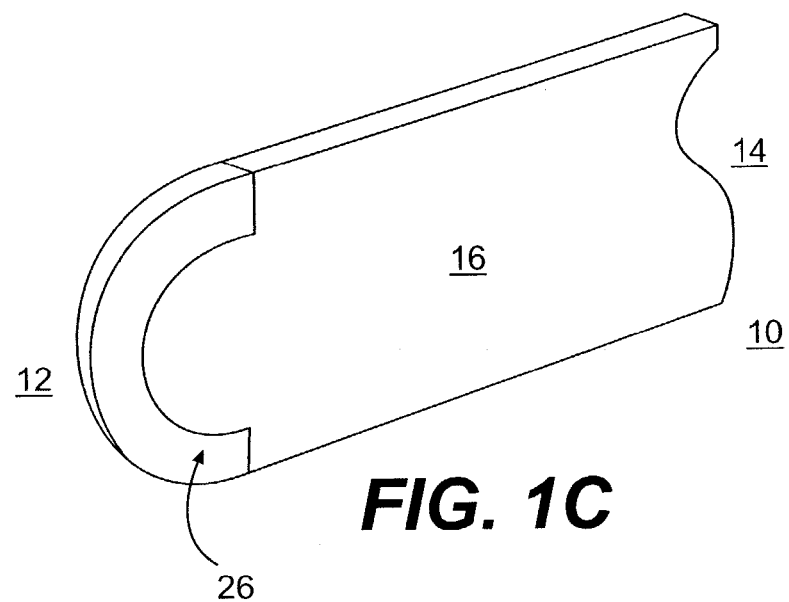

The elongated body 16 as illustrated in FIG. 1A comprises a plurality of optical fibers 20 that are held in axial alignment with respect to each other by an outer cladding 21. The outer cladding 21 may be an ultra-low hydroxyl, 530-540 nm of polyimide or material of similar performance characteristics. The cladding 21 holds the optical fibers 20 in a fixed position with respect to each other creating a multi-axial relationship. In another embodiment, the elongated body 16 depicted in FIG. 1B comprises an optical fiber 24 that is uniquely manipulated to a flattened wedged shape at the first end 12. FIG. 1C illustrates a further embodiment of penetration apparatus 10 comprising a laser light source that may be a thermoelectric detailing 26 derivative of Applicants U.S. Pat. No. 6,248,118 B1 incorporated herein by reference. The treatment-specific incision 300 may also be formed by a Holmium-Yag laser or a piezoelectric device.

Figure 1E:
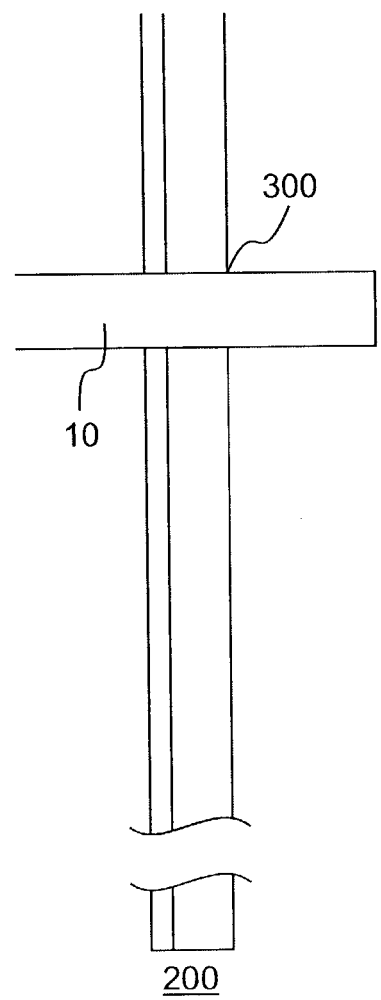
FIG. 1E is a planar view of the various placements of the treatment specific incision made by the present invention within the vessel matrix.
Figure 1D:
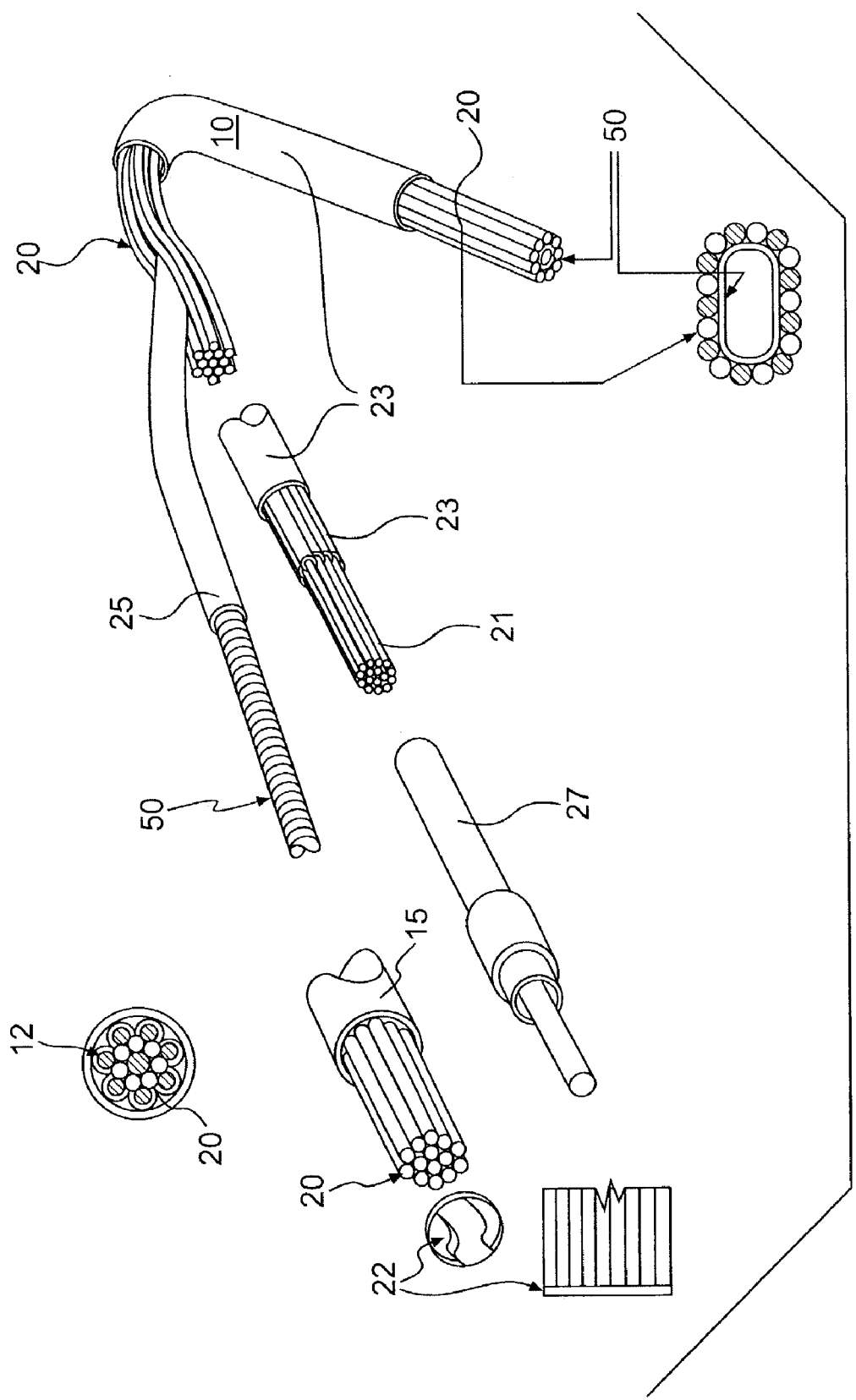

FIG. 1D illustrates the penetration apparatus 10 that comprises a first end 12 and either a second end 14 having detailing that combines a plurality of small diameter optical fibers 20 which have been fused together via their cladding or a second end 15 having detailing that combines a plurality of small diameter optical fibers 20 by way of a window or lens 22. The individual optical fibers 20, which are free to move within the outer catheter are parted at an intermediate positioning along their length to enable the introduction of the penetration apparatus 10 into their midst, are later recombined and ultimately attached by their buffer layer about a thin sleeve to form first end 12 containing a fastener 50.

The penetration apparatus 10 illustrated in FIG. 1E may be engaged to extend and retract particularly the first end 12, may be advanced through a vessel matrix 200. The vessel matrix 200 can be any combination of tissues, vessels, grafts or mixture thereof. Each of the alternative embodiments of the present invention 10 creates an incision 300 within the vessel matrix as apposed to a treatment specific hole. The incision 300 offers the benefit of removing less vessel Imatrix material and may decrease post surgical recovery time. A central longitudinal axis 18 bisects the elongated body 16. The longitudinal axis 18 serves as a guide for placement of the treatment specific incision 300 within the vessel matrix 200. The longitudinal axis 18 accommodates horizontal, vertical or angled placement of the treatment specific incision 300 in relation to the vessel matrix 200.

Fastener

Figure 2A:
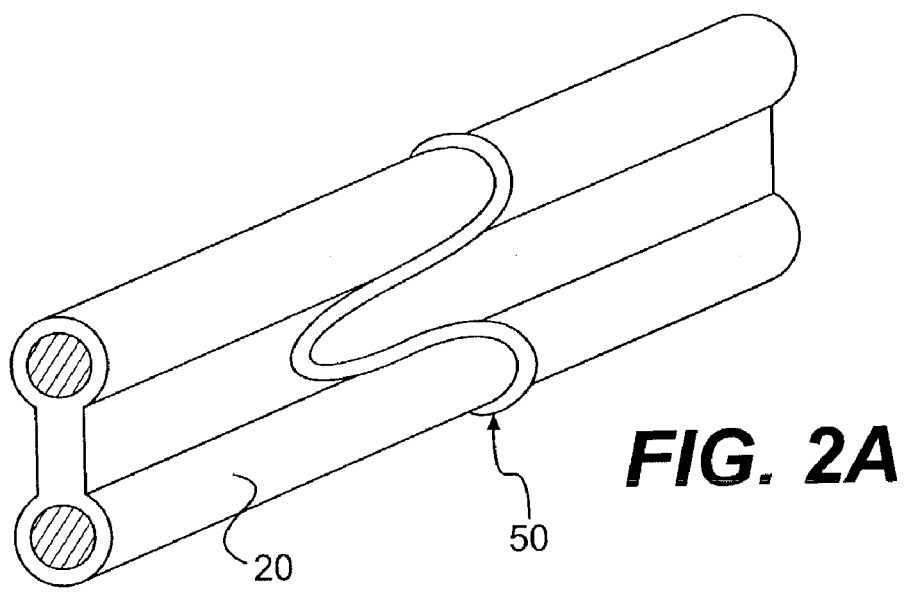
FIGS. 2A, 2C and 2D are perspective views of preferred embodiments of the penetration apparatus coupled with at least one fastener.
Figure 2B:
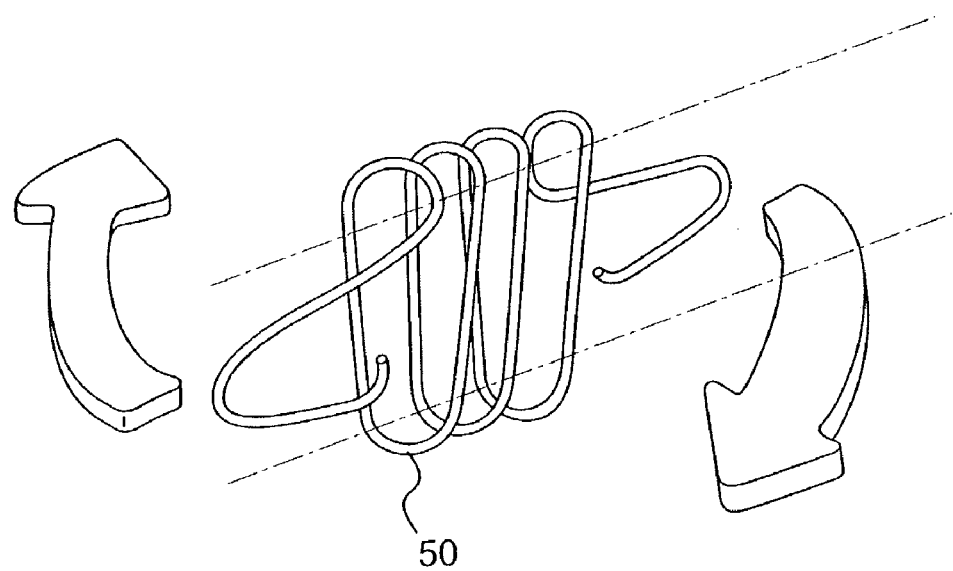
FIG. 2B illustrates the reformation of fastener as illustrated in FIG. 2A when deployed by the removal of the penetration apparatus from within its center.
Figure 2C:
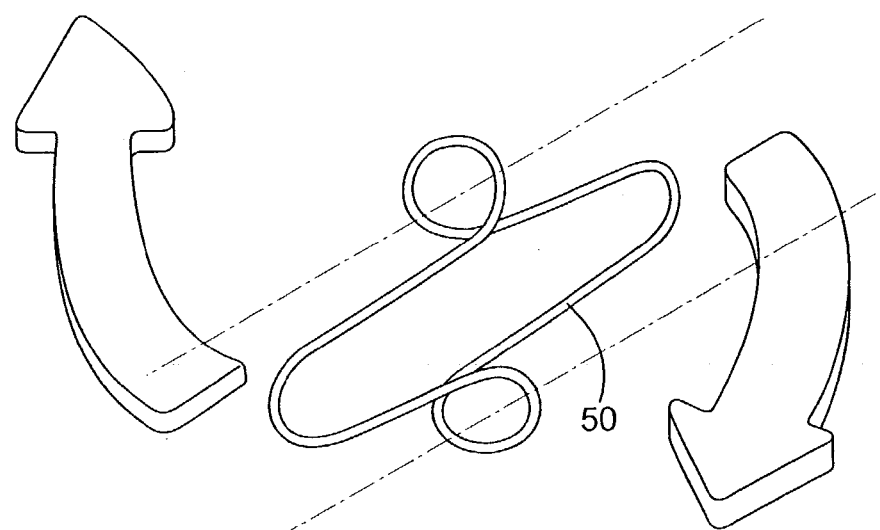
Figure 4A:
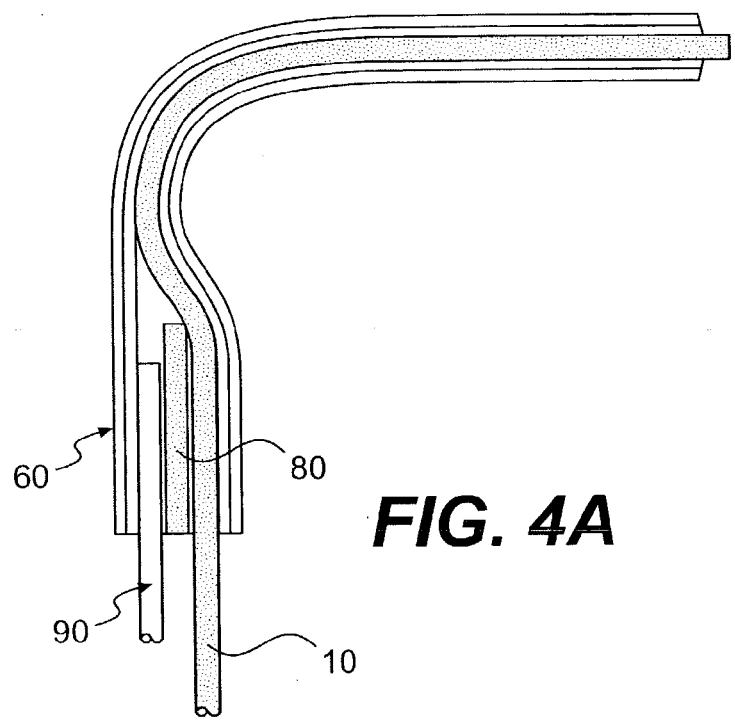
FIGS. 4A and 4B are sectional views illustrating relative positioning of the catheter derivative within the vessel matrix.
Figure 4B:
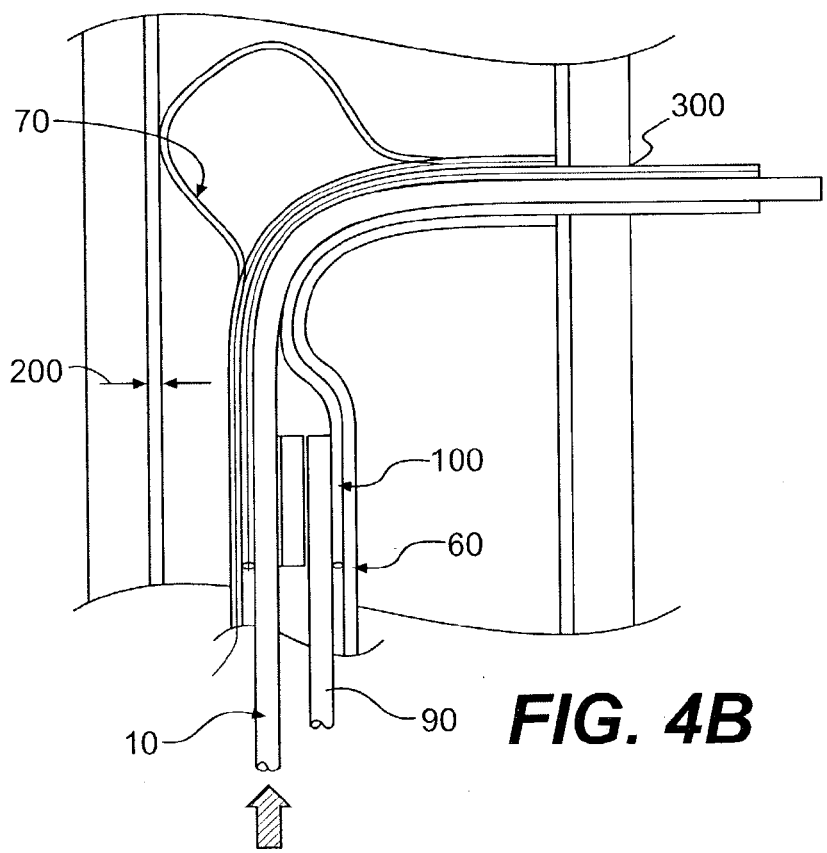

FIGS. 2A, 2B and 2C depict at least one fastener 50 that is positioned about the penetration apparatus 10. The fastener 50 may be coupled with the penetration apparatus 10 or may be a separate assembly 90, as illustrated in FIGS. 4A and 4B. The penetration apparatus 10 and the fastener assembly 90 may each be capable of housing and deploying at least one fastener; reference is made herein to at least one such embodiment. A fastener, or plurality of fasteners 50 may be deployed through the incision 300 made by a multi-axial penetration apparatus 10 to secure the vessel matrix 200.

In a preferred embodiment, the fastener 50 is formed from Nitinol or stainless steel wire, or any other procedure-appropriate material. The fastener 50 may be positioned about the elongated body 16 as illustrated in FIGS. 2A, 2B, and 2C. The fastener 50 correlates with the elongated body 16 which is either on or aligned with the central longitudinal axis 18, as illustrated in FIG. 1A. In a preferred embodiment, the fastener 50 is positioned about the elongated body 16 enabling its compact packaging for delivery to and through the treatment specific incision 300. Fasteners 50 may also be sequentially loaded for deployment at the site of the incision 300 or for varying placements within the vessel matrix. Further, the fastener 50 may be in a splayed configuration along both sides of the elongated body 16, as illustrated in FIG. 1A. Upon withdrawal of the penetration apparatus 10 from the vessel matrix, the fastener 50 deploys spanning the incision 300 and vessel matrix 200, creating increased resistance to its removal.

Figure 2D:
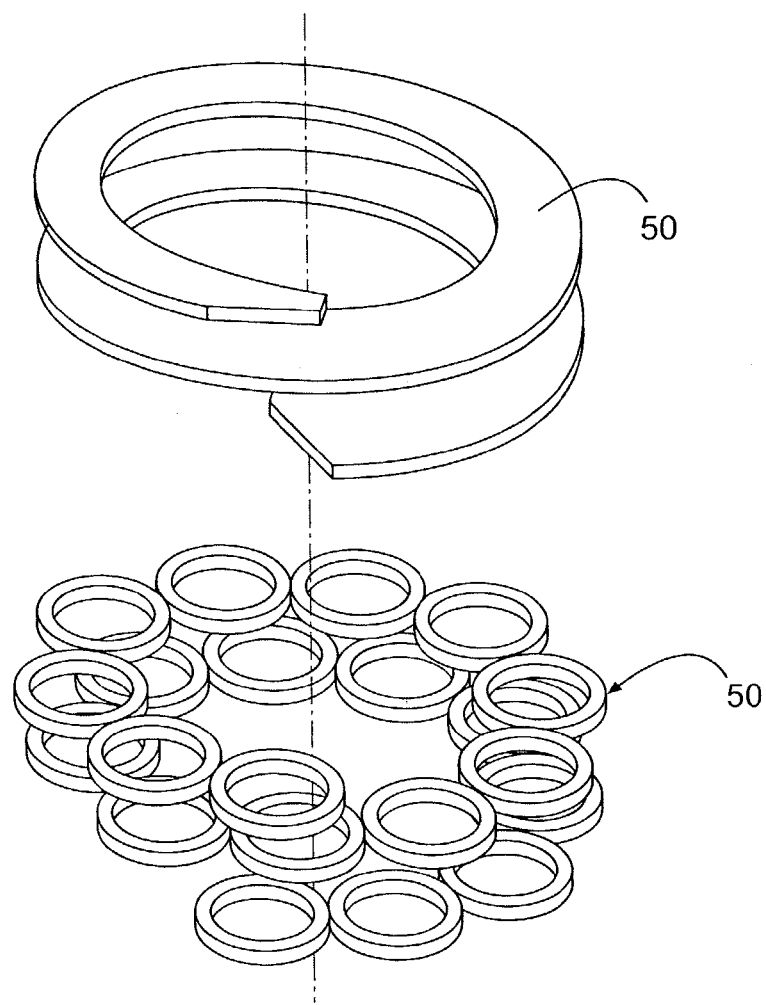

With particular reference to the fastener 50 illustrated in FIG. 2D, the fasteners coils are radially disposed about the longitudinal axis 18, when in their relaxed condition. When in their insertion-ready condition, the axially wound, canted coils of the fastener 50 are linearly aligned as indicated in FIG. 2E enabling their ganged positioning. The fastener's 50 axially wound coils in contradistinction to radial wound; enable its compact packaging for delivery to the treatment incision 300.

Catheter Derivative

In a preferred embodiment of the present invention, a derivative of the catheter disclosed in U.S. Pat. No. 6,270,516, which is incorporated herein by reference, is adapted to accommodate the penetration apparatus 10. With reference to FIG. 3A, the catheter derivative 60 also includes a cavity 64 at its center that may correspond with, or that slideably houses the penetration apparatus 10. A circular profiled catheter derivative 60 also may comprise a braided-wire reinforcing means within its outer wall 62, or any other suitable reinforcing means. The outer wall section 62 contains a plurality of lumen 66 that are able to receive an apposition device 70 and an articulation device 68 or both.

Figure 3B:
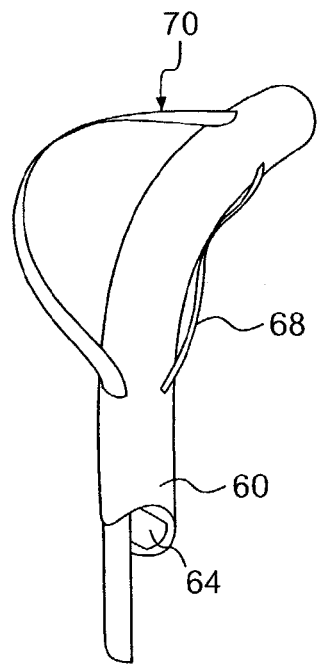
FIGS. 3B and 3C are perspective views illustrating the catheter derivative illustrated in FIG. 3A incorporating an apposition device and an articulation device for the placement of the catheter derivative.
Figure 3C:
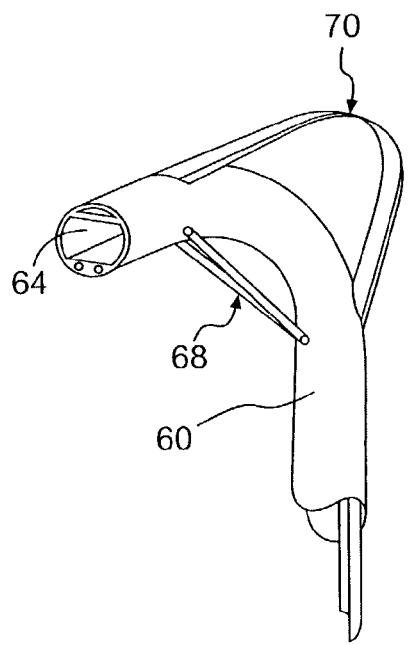

The apposition device 70, illustrated in FIGS. 3B and 3C, of a preferred embodiment of the present invention is a compact strip spring fabrication, or any other procedure-appropriate flexible material that enables the firm, intermittent positioning of the catheter derivative 60 within the vessel matrix 200. Generally, the apposition device 70 positions the catheter derivative 60 within the vessel matrix 200. The articulation device 68 of a preferred embodiment of the present invention may comprise one or more, or preferably dual wires, which may be braided, that is slideably housed within the catheter 60 and may be equispaced about the vertical centerline. The articulation device 68 angularly aligns the catheter derivative 60 with the vessel matrix 200. In an alternative preferred embodiment, the articulation device 68 may not be necessary due to the functioning of the apposition device 70 that bends the catheter derivative 60 around a pre-determined arc effectively creating articulation and apposition in one adjustment.

FIGS. 4A and 4B illustrate a catheter derivative 60 in which the penetration apparatus 10 and the fastener assembly 90 are accommodated for sequential introduction. The penetration apparatus 10 and the fastener assembly 90 may be separated by a divider 80. The divider 80 partitions the cavity 64 within the catheter derivative's generic profile. At the point of articulation, a single cavity is formed. The sequential insertion of the penetration apparatus 10 and the fastener assembly 90 both nullifies the potential for surface damage to the optical fiber by overlying fasteners and reduces the incision created by the penetration apparatus 10.

FIG. 4B illustrates a thin-walled sheath 100 which slideably lines the cavity 64 of the catheter derivative 60 providing a retractable conduit through which the penetration apparatus 10 and in an embodiment, the fastener assembly 90 may be sequentially made to traverse the vessel matrix 200. The remotely controlled, selectively engaged, retractable sheath 100 surrounding the penetration apparatus 10 at the time of its insertion through the vessel matrix 200, as illustrated in FIG. 4A, becomes at its removal, a lubricious tubulation through which the fastening assembly accesses the outer vessel matrix 200, illustrated in FIG. 4B. The sequential insertion of the penetration apparatus 10 and the fastener assembly 90 into the vessel matrix 200 through the retractable sheath both nullifies the potential for surface damage to the penetration apparatus 10 by overlaying fasteners and reduces the size of treatment specific incision 300 required for fastener placement. When the penetration apparatus 10 comprises at least one optical fiber the reduced fiber diameter when working collaboratively with fastener assembly 90 forms a smaller, more flexible catheter derivate 60.

In forming a treatment specific incision, the penetration apparatus 10 is delivered to the surgical site through a catheter derivative 60 or otherwise appropriate medium. The catheter 60 is positioned adjacent to the matrix 200 by adjustment of its apposition and/or articulation devices. Once appropriately positioned within the vessel, the penetration apparatus 10 and retractable sheath 100 are advanced through the vessel matrix 200 forming a treatment specific incision 300. The dimensions of the treatment specific incision correspond to the dimensions of the first end 12 of the penetration apparatus or may correspond to the thin walled sheath 100 of the catheter derivative 60. Following the incision in the vessel matrix 200, the penetration apparatus 10 is withdrawn to the point of catheter articulation. The fastening assembly 90 is now advanced through the sheath 100 and then deployed within the matrix 200 with retraction or the actuation of the fastener assembly 90. The deployed fastening assembly 90 resumes its relaxed configuration so holding elements of the vessel matrix 200 in a compressed relationship.

In accordance with another method for the placement of fasteners 50 of the present invention, a treatment conduit is created when a catheter derivative 60 is appropriately positioned for a surgical procedure, the conduit extending between the point of proximal access, such as the femoral, groin, axillary, or brachial artery, to a distally positioned surgical site. At least one fastener 50 is positioned around, within, or in conjunction with a penetration apparatus 10 and an incision 300 is formed through the vessel matrix 200 with the penetration apparatus 10. Intraluminal access to an adventitial tissue layer is so gained, facilitating attachment of at least one fastener 50 to the intraluminal side of a repair member and the adventitial tissue layer (the vessel matrix 200). The fastener 50 is deployed by removing the penetration apparatus 10 from within, about, or by the removal of related dispensing/packaging details. In accordance with this method, the penetration apparatus 10 may comprise a single optical fiber or a bundle of optical fibers 24; it may also comprise a thermo-electric device 26. The aperture may be formed by a laser, thermoelectric or piezoelectric device.

Numerous characteristics and advantages have been set forth in the foregoing description, together with details of structure and function. The novel features are pointed out in the appended claims. The disclosure, however, is illustrative only, and changes may be made in detail, especially in matters of shape, size and arrangement of parts, within the principle of the invention, to the full text indicated by the broad general meaning of the terms in which the appended claims are expressed.

It will be apparent to those skilled in the art that variations and modifications of the present invention can be made without departing from the scope or spirit of the invention. For example, the present invention is not limited to securing a surgical component to a vessel matrix that may be a graft, tissue or mixture thereof. Rather, it is contemplated that the present invention may be used in connection with securing a vessel to another vessel, tissue-to-tissue, surgical components to surgical components, and any variation thereof. Thus, it is intended that the present invention cover all such modifications and variations provided they come within the scope of the appended claims and their equivalents.

What is claimed is:

1. A penetration apparatus for use during a surgical procedure, comprising:
   a thin elongated body having a first end, a second end, and a central longitudinal axis;
   the first end opposes the second end on the body, and is aligned with a vessel matrix during the surgical procedure;
   the second end is substantially free;
   the longitudinal axis spans the body from the first to the second end wherein the body rotates around the axis for placement of an incision within the vessel matrix;
   a first optical fiber and a second optical fiber, the first optical fiber is located above the central longitudinal axis and the second optical fiber is located below the central longitudinal axis and an outer cladding disposed between the first and second optical fibers wherein the outer cladding axially joins the first and the second optical fibers.

2. The penetration apparatus of claim 1, wherein the thin elongated body is oblong.

3. The penetration apparatus of claim 1, wherein the elongated body further comprises at least one optical fiber.

4. The penetration apparatus of claim 1, wherein the first end is flattened.

5. The penetration apparatus of claim 4, wherein the second end is flattened.

6. The penetration apparatus of claim 5, wherein the elongated body is attached to a laser light source.

7. The penetration apparatus of claim 6, wherein the laser light source comprises a Holmium Yag.

8. The penetration apparatus of claim 1, wherein the elongated body further comprises a piezoelectric device.

9. The penetration apparatus of claim 1, further comprising at least one fastener coupled with the elongated body.

10. The penetration apparatus of claim 9, wherein the fastener corresponds with the elongated body.

11. The penetration apparatus of claim 1, further comprising a fastener assembly having at least one fastener.

12. A catheter derivative for use during a surgical procedure, comprising:
    a catheter with at least one cavity;
    a penetration apparatus comprising a thin elongated body having a first end, a second end and a central longitudinal axis; the first end opposes the second end and is aligned with a vessel matrix during the surgical procedure; the second end is substantially free; and the longitudinal axis spans the body from the first end to the second end wherein the body may rotate around the axis for placement;
    wherein the penetration apparatus is slideably housed within the cavity of the catheter;
    a first optical fiber and a second optical fiber, the first optical fiber is located above the central longitudinal axis and the second optical fiber is located below the central longitudinal axis and an outer cladding disposed between the first and second optical fibers wherein the outer cladding axially joins the first and the second optical fibers.

13. The catheter derivative of claim 12, wherein the catheter further comprises an articulation device for angular placement.

14. The catheter derivative of claim 12, wherein the catheter further comprises an apposition device for placement within the vessel matrix.

15. The catheter derivative of claim 12, wherein the catheter further comprises an articulation device for placement within the vessel and an apposition device for angular placement.

16. The catheter derivative of claim 12, wherein the cavity corresponds with the penetration apparatus.

17. The catheter derivative of claim 12, wherein the elongated body is oblong.

18. The catheter derivative of claim 12, wherein the elongated body further comprises at least one optical fiber.

19. The catheter derivative of claim 12, wherein the first end is flattened.

20. The catheter derivative of claim 19, wherein the second end is flattened.

21. The catheter derivative of claim 12, wherein the elongated body is attached to a laser light source.

22. The catheter derivative of claim 21, wherein the laser light source comprises a Holmium Yag.

23. The catheter derivative of claim 12, wherein the elongated body further comprises a piezoelectric device.

24. The catheter derivative of claim 12, further comprising at least one fastener coupled with the elongated body.

25. The catheter derivative of claim 24, wherein the fastener corresponds with the elongated body.

26. The catheter derivative of claim 12, further comprising a fastener assembly having at least one fastener.

27. The catheter derivative of claim 26, further comprising a divider interposed between the penetration apparatus and the fastener assembly.

28. The catheter derivative of claim 12, further comprising a thin-walled sheath slideably positioned therein, wherein the penetration apparatus is enclosed by the thin walled sheath and the catheter.

29. The catheter derivative of claim 28, further comprising a fastener assembly having at least one fastener.

30. The catheter derivative of claim 29, further comprising a divider interposed between the penetration apparatus and fastener assembly.

31. A method of using a penetration apparatus during a surgical procedure which comprises the steps of:
providing a thin elongated body having a first end, second end, and a central longitudinal axis; the first end opposes the second on the body and is aligned with a vessel matrix during the surgical procedure; the second end is substantially free; the longitudinal axis spans the body from the first to the second end wherein the body rotates around the axis for placement of an incision within the vessel matrix; a first optical fiber and a second optical fiber, the first optical fiber is located above the central longitudinal axis and the second optical fiber is located below the central longitudinal axis and an outer cladding disposed between the first and second optical fibers wherein the outer cladding axially joins the first and the second optical fibers;
positioning the penetration apparatus within the vessel matrix; and
activating and advancing the penetration apparatus to form an incision in the vessel matrix.

32. The method of using the penetration apparatus of claim 31, further comprising the step of coupling a fastener to the penetration apparatus wherein the fastener surrounds a cross section of the penetration apparatus prior to positioning the penetration apparatus; and
deploying the fastener through the incision in the vessel matrix after activating the penetration apparatus.

33. A method of using a penetration apparatus with a catheter derivative during a surgical procedure which comprises the steps of:
providing a thin elongated body having a first end, second end, and a central longitudinal axis; the first end opposes the second on the body and is aligned with a vessel matrix during the surgical procedure; the second end is substantially free; the longitudinal axis spans the body from the first to the second end wherein the body rotates around the axis for placement of an incision within the vessel matrix; a first optical fiber and a second optical fiber, the first optical fiber is located above the central longitudinal axis and the second optical fiber is located below the central longitudinal axis and an outer cladding disposed between the first and second optical fibers wherein the outer cladding axially joins the first and the second optical fibers;
inserting the penetration apparatus into the catheter;
positioning the catheter within the vessel matrix;
activating and advancing the penetration apparatus through the catheter in the vessel matrix; and
withdrawing the penetration apparatus.

34. The method of claim 33, further comprising advancing a thin walled sheath of the catheter derivative through the vessel matrix prior to activating and advancing the penetration apparatus.

35. The method of claim 33, wherein the penetration apparatus has at least one fastener, which further comprises the step of deploying the fastener through an incision in the vessel matrix prior to withdrawing the penetration apparatus.

36. The method of claim 33, wherein the catheter derivative has a fastener assembly, which further comprises the step of activating and advancing the fastener assembly through the catheter after withdrawing the penetration apparatus; and deploying a fastener through an incision in the vessel matrix.

37. A method of placing at least one fastener during a surgical procedure fasteners which comprises the steps of:
providing a thin elongated body having a first end, second end, and a central longitudinal axis; the first end opposes the second on the body and is aligned with a vessel matrix during the surgical procedure; the second end is substantially free; the longitudinal axis spans the body from the first to the second end wherein the body rotates around the axis for placement of an incision within the vessel matrix; a first optical fiber and a second optical fiber, the first optical fiber is located above the central longitudinal axis and the second optical fiber is located below the central longitudinal axis and an outer cladding disposed between the first and second optical fibers wherein the outer cladding axially joins the first and the second optical fibers;
gaining access to a surgical site with a catheter derivative;
positioning the catheter derivative within the vessel matrix;
inserting a penetration apparatus into the catheter;
activating and advancing the penetration apparatus to form a treatment specific incision in vessel matrix; and
deploying a fastener through the incision of the vessel matrix.

38. The method of claim 37, further comprising the step of inserting a fastener assembly into the catheter after inserting the penetration apparatus; withdrawing the penetration apparatus prior to deploying the fastener; and activating and advancing the fastener assembly within the vessel matrix.

* * * * *